(12) United States Patent
Miller et al.

(10) Patent No.: US 7,112,357 B2
(45) Date of Patent: *Sep. 26, 2006

(54) MEDICAL DEVICES COMPRISING A MULTILAYER CONSTRUCTION

(75) Inventors: Paul Miller, St. Paul, MN (US); Yigun (Bruce) Wang, Maple Grove, MN (US); Chaunting You, Brooklyn Park, MN (US); Edward Parsonage, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/055,743

(22) Filed: Jan. 23, 2002

(65) Prior Publication Data

US 2003/0138582 A1    Jul. 24, 2003

(51) Int. Cl.
*B29D 22/00* (2006.01)
*B29D 23/00* (2006.01)
*B32B 7/08* (2006.01)

(52) U.S. Cl. .............. 428/36.92; 428/500; 428/476.9; 604/96.01

(58) Field of Classification Search ............ 428/39.91, 428/35.7, 36.9, 36.92, 500, 476.7; 604/96.01
See application file for complete search history.

(56) References Cited

U.S. PATENT DOCUMENTS

| 4,265,848 | A | | 5/1981 | Rusch .................. 264/130 |
| 4,602,058 | A | * | 7/1986 | Graham et al. ............ 524/320 |
| 4,886,689 | A | * | 12/1989 | Kotliar et al. ............. 428/35.7 |
| 5,195,969 | A | | 3/1993 | Wang et al. ................ 604/96 |
| 5,270,086 | A | | 12/1993 | Hamlin .................... 428/35.2 |
| 5,478,320 | A | | 12/1995 | Trotta ....................... 604/96 |
| 5,503,631 | A | | 4/1996 | Onishi et al. ................ 604/96 |
| 5,538,510 | A | | 7/1996 | Fontirroche et al. ........ 604/265 |
| 5,567,203 | A | | 10/1996 | Euteneuer et al. ............ 604/96 |
| 5,587,125 | A | | 12/1996 | Roychowdhury ........... 264/515 |
| 5,620,649 | A | | 4/1997 | Trotta ........................ 264/515 |
| 5,769,817 | A | | 6/1998 | Burgmeier .................... 604/96 |
| 5,789,047 | A | | 8/1998 | Sasaki et al. .............. 428/36.91 |
| 5,820,594 | A | | 10/1998 | Fontirroche et al. .......... 604/96 |
| 5,824,173 | A | | 10/1998 | Fontirroche et al. .......... 156/86 |
| 5,833,657 | A | | 11/1998 | Reinhardt et al. ............ 604/96 |
| 5,879,369 | A | | 3/1999 | Ishida ........................ 606/194 |
| 5,961,545 | A | | 10/1999 | Lentz et al. .................... 623/1 |
| 6,004,310 | A | | 12/1999 | Bardsley et al. ............. 604/524 |
| 6,010,521 | A | | 1/2000 | Lee et al. .................... 606/194 |
| 6,087,442 | A | * | 7/2000 | LaFleur et al. ................ 525/57 |
| 6,124,007 | A | | 9/2000 | Wang et al. ................ 428/35.2 |
| 6,132,824 | A | | 10/2000 | Hamlin ...................... 428/35.2 |
| 6,165,166 | A | | 12/2000 | Samuelson et al. ......... 604/524 |
| 6,193,686 | B1 | | 2/2001 | Estrada et al. ......... 604/103.09 |
| 6,242,063 | B1 | | 6/2001 | Ferrera et al. ............. 428/35.2 |
| 6,277,093 | B1 | | 8/2001 | Lee ............................. 604/96 |
| 6,284,333 | B1 | | 9/2001 | Wang et al. ................ 428/35.5 |
| 6,299,596 | B1 | | 10/2001 | Ding ....................... 604/96.01 |
| 6,319,228 | B1 | | 11/2001 | Kastenhofer ............. 604/96.01 |

(Continued)

FOREIGN PATENT DOCUMENTS

EP    0803264    12/2002

(Continued)

*Primary Examiner*—Michael C. Miggins
(74) *Attorney, Agent, or Firm*—Vidas, Arrett & Steinkraus P.A.

(57) ABSTRACT

A medical device comprising a first substrate, a second substrate and a powder coated tie layer between the first and second substrates resulting in a multilayer construction.

10 Claims, 3 Drawing Sheets

U.S. PATENT DOCUMENTS

| | | |
|---|---|---|
| 6,328,925 B1 | 12/2001 | Wang et al. ................. 264/512 |
| 6,358,227 B1 | 3/2002 | Ferrera et al. ......... 604/103.06 |
| 2004/0158256 A1* | 8/2004 | Chen et al. ................... 606/96 |

FOREIGN PATENT DOCUMENTS

| WO | WO 01/81808 | 11/2001 |
|---|---|---|

* cited by examiner

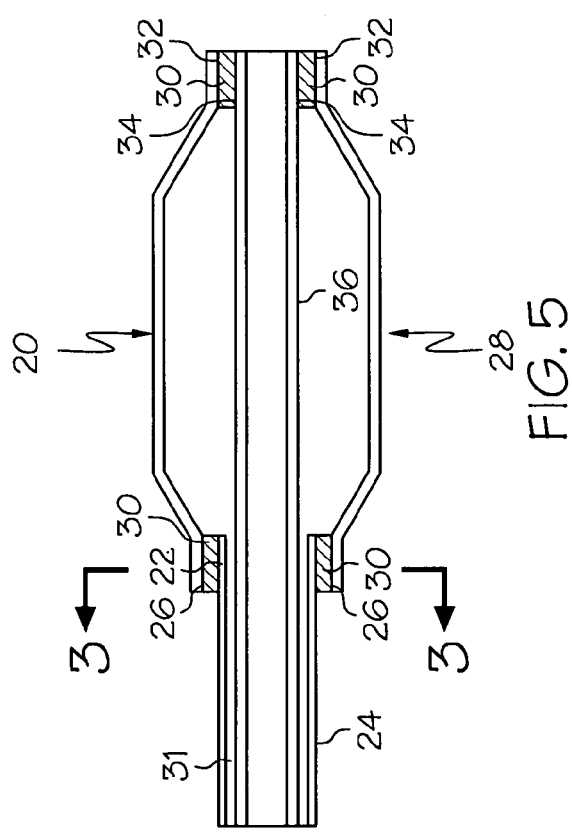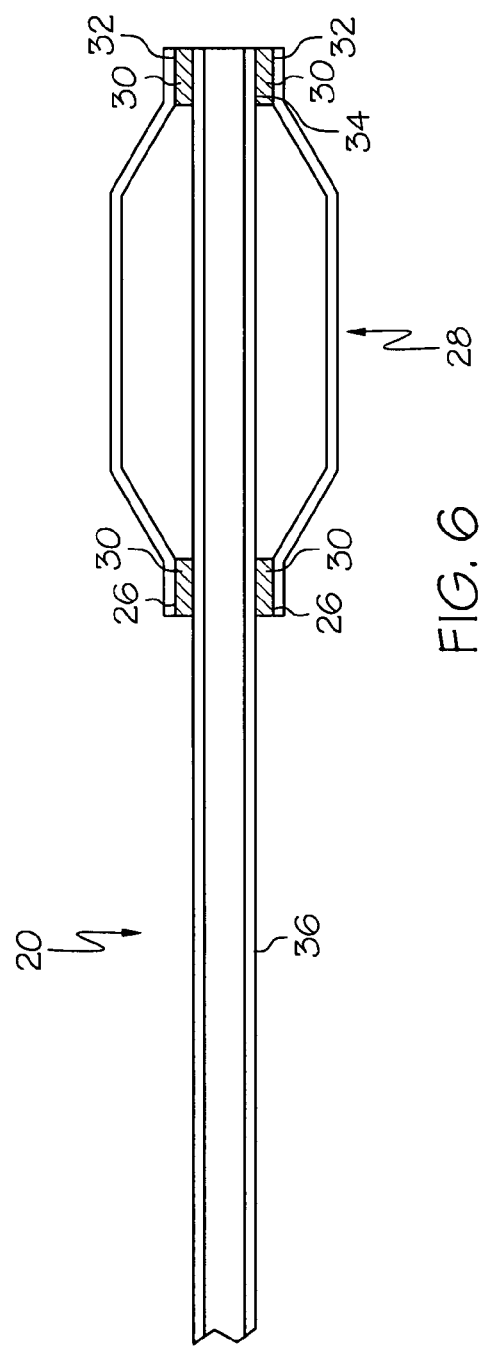

MEDICAL DEVICES COMPRISING A MULTILAYER CONSTRUCTION

FIELD OF THE INVENTION

The present invention relates to tubing having a multilayer construction which may be incorporated into medical devices such as catheters. The construction includes an adhesive or tie layer for adhering different materials together.

BACKGROUND OF THE INVENTION

Intraluminal medical devices designed for use in treating vascular diseases are often inserted into the vasculature of a patient at a point remote from the treatment site. For instance, an intravascular catheter may be introduced into the femoral artery through an incision in the groin area, and is then advanced through the femoral artery to the coronary treatment site. The vessels through which the catheter travels are small and the passage through the vessel is tortuous making positioning of the catheter difficult, and can be quite often uncomfortable for the patient. It is therefore desirable to make this procedure as atraumatic to the patient as possible. This, consequently, requires the catheter to have specific performance characteristics. These characteristics include lubricity, trackability, pushability, and so forth. However, while the catheter requires a certain amount of flexibility in order to have good maneuverability and trackability through the vessels, it must also be sufficiently strong in the longitudinal direction so as not to buckle or kink when crossing lesions. Also, balloon catheters require that the walls be made of a sufficiently strong material to withstand rupture because they are inflated under extremely high pressure.

In order to achieve a combination of the desired properties, more than one type of material may therefore be employed in the construction of a catheter. The construction may therefore involve bonding or fusing together of various parts through the use of adhesives, or through a welding process, for instance. An example is one in which a dilatation balloon is adhered or fused to a catheter shaft. The balloon and catheter outer shaft materials must therefore be of a bondable nature.

Polymeric materials that are not inherently lubricious are typically more easily bonded. However, this also makes insertion and maneuverability of the catheter more difficult. Therefore, if the polymer is not lubricious in nature, lubricants are often added to the outer surface. Use of lubricants, however, also complicate the bonding process.

Further, the inner surfaces of tubing used in intraluminal devices must also meet certain performance criteria. For instance, the inner surface of a catheter shaft must produce low surface friction when in contact with the guidewire. This low surface friction facilitates advancement of the catheter over the guidewire, for instance. This can also be accomplished, for example, by the use of lubricious coatings, such as polytetrafluoroethylene (PTFE) which has been used as a coating on the inner lumen surface of a catheter shafts.

It is difficult to find one material that meets all of the performance requirements. Therefore, it is often also desirable to manufacture tubing for medical devices that have more than one layer of material. This too involves adhering or fusing together of the layers.

Multilayered tubing has been used to provide medical tubing with the combination of desirable properties. For instance, U.S. Pat. No. 6,165,166 provides a coextruded flexible tubing. The multilayer structure comprises a core layer of a lubricious polymeric material, an outer layer comprising directly bondable polymer, and an intermediate tie layer comprising a polymer having a pendant functionality capable of adhering the lubricious material of the core layer to the directly bondable material of the outer layer. The intermediate tie layer provides a strong connection between the core layer and the outer layer.

SUMMARY OF THE INVENTION

The present invention relates to a multilayer construction of substrates or tubular members useful in medical devices, and to a method of making the same. The multilayer structure includes a powder coated layer provided between at least two substrates which may be of the same or a different material. The powder coated layer may be provided continuously along the substrate or only in discrete, non-continuous locations along the substrate.

In some embodiments a first substrate is comprised of a first material and a second substrate is comprised of a second material different from the first material. The powder coating layer operates to provide an adhesive layer between the two substrates.

In another aspect, the present invention relates to a process for assembling medical devices that are manufactured of at least two substrates or tubular members. In some embodiments, a first substrate or tubular member is formed of a first material and a second substrate or tubular member is formed of a second material different from the first material. The method includes application of a powder coating layer between the parts for adhering the substrates or tubular members together.

The powder coating may also include a blend of at least two different polymeric materials, one of which is compatible with the first material and one of which is compatible with the second material.

The present invention further relates to tubular members for use in medical devices in which the tubular members have multiple layers. The multiple layers may extend along the entire length of the tubing, or the multiple layers may be located in predetermined, discrete areas of the tubing.

BRIEF DESCRIPTION OF THE FIGURES

FIG. 5 is a side view of a catheter assembly which includes the multilayer tubular construction of the present invention.

FIG. 6 is a catheter assembly illustrating an alternative embodiment to that shown in FIG. 5.

DETAILED DESCRIPTIONS OF THE PREFERRED EMBODIMENTS

Figure 1:
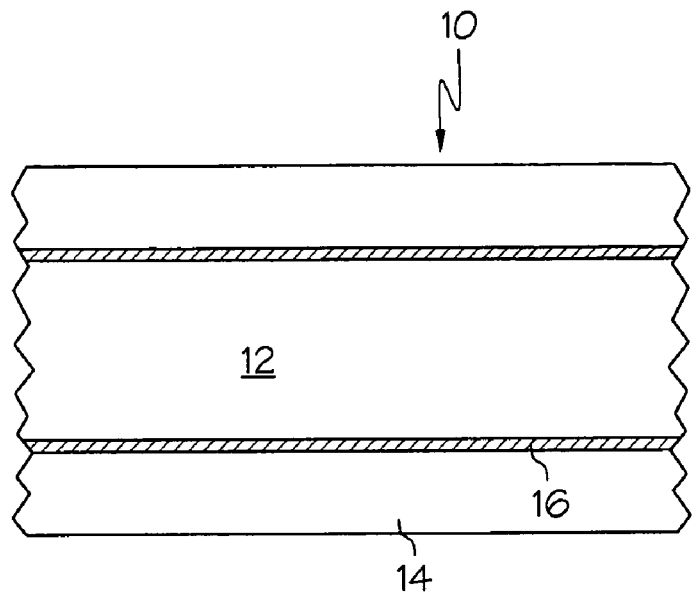
FIG. 1 is a side view of one embodiment of the multilayer structure of the present invention.

The present invention relates to a medical device including a multilayer construction comprising at least two substrates or at least two tubular members in which at least one intermediate layer is a powder coating layer. The powder coating may be applied along the entire length of the substrates or tubular members, or may be applied in discrete locations along the entire length of the substrates or tubular members. In some embodiments, the powder coating acts as a tie layer to adhere two different substrates together.

As used herein, the term "adhered" refers to a state in which two surfaces are held together. In the present invention, a powder coating layer may be applied to hold at least two substrates together. The powder coating may be heated during application to a first substrate and the second substrate to which it is to be adhered immediately joined to the first substrate, or the powder coating may be reheated at some point in the future when it is desirable to join the substrates. In this sense, the method of the present invention offers flexibility as to when the substrates are joined together. The powder coating may be heated using a laser beam, or some other radiant or thermal source of energy, at the time of joining of the two substrates whether immediately upon application of the powder coating or at a later time, so that the powder coating composition is flowable or molten. The powder coating may be partially or completely melted as desired.

The present invention is suited for all types of medical devices. In some embodiments, the invention can be advantageously applied to tubular medical devices including, for example, balloons, balloon catheters, guide catheters, stent delivery systems, and so forth.

An alternative method to that described above is to employ a grounded metallic holder for the substrate or article. For instance, in the present invention, when a tubular polymeric substrate is employed, a grounded metal mandrel may be inserted within the inner lumen of the tubular member. The tubular polymeric member can then be exposed to a charged powder in the presence of an applied electric field to produce the desired coating. The exposure may be through the use of a spray nozzle, for instance, or through the use of a fluidized bed of powder coating. A second tubular member is then placed over the powder coated region, and thermal energy applied to the overlapping region of the two tubular members.

Alternatively, the grounded metal mandrel may be exposed to a charged powder in the presence of an applied electric field. A section of tubing may then be overlapped with the powder coated region of the grounded metal mandrel. This section is then thermally annealed resulting in a coating on the inner surface of the tubular member. A second tubular member is then inserted into the first and the section wherein the powder coated first tubular member and the second tubular member overlap is thermally annealed.

Using the powder coating method of the present invention allows construction of tubing that may have multiple layers along the entire length of the tubing, but also allows multiple layers to be selectively placed in discrete, predetermined locations along the tubing. The method thus offers an advantage over formation of multilayer tubing using coextrusion techniques which make formation of multiple layers in discrete locations quite difficult.

If it is desirable to apply the powder coating layer in only discrete locations, the substrate may be masked off to prevent applying the powder coating to other areas of the substrate.

The present invention may be employed to form a multilayer structure by overlapping of substrates, sometimes referred to in the industry as a "lap" weld, or it may be employed to form a multilayer structure by joining substrates adjacently, sometimes referred to in the industry as a "butt" weld. If desired, both types of joints may be employed at different locations along the tube.

As used herein, the term "lap joint" shall refer to a joint in which the ends or edges of the substrates are overlapped and adhered together.

As used herein, the term "butt joint" shall refer to the joining of substrates end to end.

A butt weld may be accomplished by inserting a metal mandrel through a first tubular member so that the mandrel extends just beyond the end of the tubular member thus exposing a section of mandrel. The mandrel is then exposed to a charged powder coating, the result being that the powder coating is selectively brought into contact with the end of the first tubular member. A second tubular member is inserted over the end of the mandrel until it is in contact with the end of the first tubular member. This assembly is then exposed to thermal energy and annealed.

The present invention may thus find utility in the assembly of various medical devices employing tubular structures including catheter assemblies. Examples of applications in which the present invention may be employed in the formation of a catheter assembly include, but are not limited to, joining the distal tip the distal end of the inner shaft, joining the distal tip to a dilatation balloon, joining a dilatation balloon to the inner shaft, joining a dilatation balloon to the outer shaft, joining marker bands to the inner shaft, joining the proximal inner shaft to the distal inner shaft, joining the proximal outer shaft to the distal outer shaft, joining a metal hypotube to the distal outer shaft, joining a manifold to the proximal inner shaft and/or proximal outer shaft, joining an inner shaft to an outer shaft, and so on and so forth.

FIG. 1 illustrates generally at 10, one embodiment of the present invention in which an inner tubular member 12, is secured to an outer tubular member 14 through a powder coated tie layer 16. In this embodiment, the tie layer is provided along the length of the tubular members thereby forming a multilayer structure. Inner tubular member 12 may be a guide wire shaft, for instance. Outer tubular member 14 may be an outer guide wire shaft or a dilatation balloon, for instance.

Figure 2:
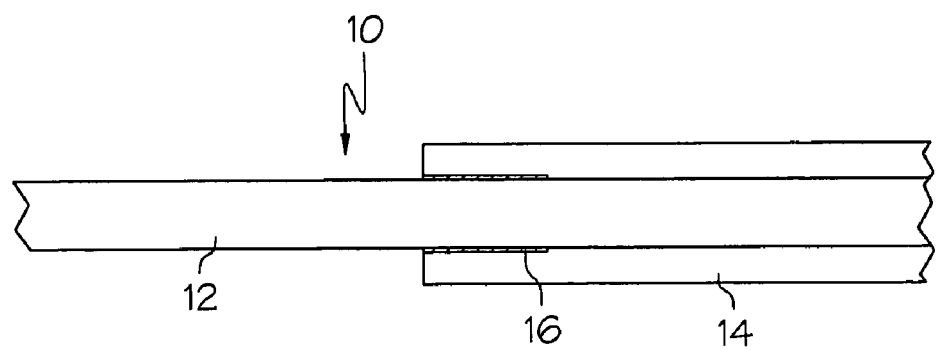
FIG. 2 is a side view of an alternative embodiment of the multilayer structure of the present invention in which the multiple layers are found in discrete locations along a substrate.

FIG. 2 illustrates an alternative embodiment in which the tie layer 16 is provided at the distal end of the inner tubular member 12 and the proximal end of the outer tubular member 14 which forms a lap joint structure. The outer tubular member may be a dilatation balloon, a catheter shaft, and so forth.

Figure 3:
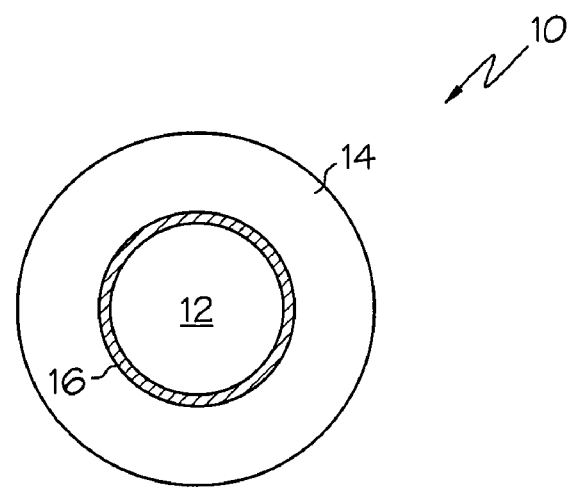
FIG. 3 is a cross-sectional view of a multilayer tubular member of the present invention.

FIG. 3 is a cross-sectional view illustrating the multilayer structure of the present invention.

Figure 4:
FIG. 4 is a side-view of one embodiment of the present invention in which a first substrate and a second substrate are joined adjacently.

FIG. 4 illustrates an alternative embodiment of the present invention in which a first tubular member 12 is adjacently connected by a butt weld to a second tubular member 14 by a powder coating layer 16.

FIG. 5 illustrates generally at 20 a catheter assembly in which the distal end 22 of an outer 24 which defines the inflation lumen 31 is joined to the proximal end 26 of dilatation balloon 28 through a powder coating layer 30. The distal end 32 of balloon 28 is joined to the distal end 34 of inner guide wire shaft 36 with a powder coating layer 30. The proximal end 26 of dilatation balloon 28 is joined to the distal end 22 of outer 24 with a powder coating tie layer 30.

In FIG. 6 a powder coating layer 30 is selectively placed in predetermined discrete locations along a single lumen catheter shaft 36 of catheter assembly 20. Powder coating 30 joins the proximal end 26 of balloon 28 to the guide wire shaft 36 and joins the distal end 32 of balloon 28 to the distal end 34 of guide wire shaft 36.

Further alternative constructions include other members, such as a hypotube, joined to a tubular catheter shaft. A hypotube may be an elongated flexible thin walled metallic tube having a small diameter of less than about 0.1 inches. Hypotubes may be manufactured of stainless steel, for instance, and may be optionally provided with a low friction coating such as polytetrafluoroethylene. Hypotubes are provided to increase the collapse strength. An example of a hypotube shaft segment connected to a hollow tubular polymeric catheter shaft is described in commonly assigned U.S. Pat. No. 5,567,203 incorporated by reference herein in its entirety. The powder coating tie layer is provided between the metallic hypotube and the polymeric catheter shaft providing improved adhesion between the two substrates.

The present invention is thus also conducive to providing discrete areas of a catheter assembly with a tie layer. A localized or discrete section of a substrate may be readily coated with the powder composition using any method known in the art. One method to selectively apply the powder coating is to employ an electrically insulating mask over a grounded substrate with portions of the mask exposed to the application of the powder coating by an electrostatic coating process. An alternative application method is to heat a localized section of a substrate and expose the section to a fluidized bed of powder coating material.

The powder coating layer may be employed between substrates which are of the same or of a different material. For example, in some embodiments wherein one of the substrates is an inner tubular member, such as an inner guide wire shaft 36 of a catheter assembly 20 as in FIGS. 5 and 6, the inner guide wire shaft may be manufactured of a first material, and the second outer member 24 may be manufactured of the same material, or may be manufactured of a second material which is different from the first.

Examples of polymeric materials suitably employed in the manufacture of the inner tubular member 36 and/or the outer member 24 include both non-elastomeric and elastomeric materials including, but not limited to, polyesters such as polyethyleneterephthalate, polyethers such as polyether-block-amides, polyether-polyesters and polyether/polyamide/polyesters, polyamides, nylons, polyurethanes including polyether urethanes, polyester urethanes and polyureas, polyolefins including low (LDPE) and high density polyethylene (HDPE), polypropylene and ethylene vinyl acetate copolymers, polymers of vinyl monomers such as polyvinylchlorides and vinylidene fluorides, fluoropolymers including PTFE, FEP, poly(meth)acrylates, polycarbonates, any copolymers thereof, and mixtures thereof.

As used herein the term "copolymers" is intended to include those polymers including two or more different monomer residues or repeat units in their structure and includes random, alternating, graft and block copolymers. One of ordinary skill in the art would understand that this list is intended for exemplary purposes only, and is not an exclusive list. There are numerous other polymers that may be employed herein.

In one particular embodiment, the inner member 36 is a thin walled construction of HDPE. The wall thickness of the material and its specific properties may depend in part upon whether the catheter shaft portion is proximally located on the catheter device (thus requiring more stiffness) or distally located on the catheter device (thus requiring a flexible material of suitable softness and modulus of elasticity).

In some embodiments, the inner guide wire shaft 36 is bonded to an outer member which may be the dilatation balloon 28 as shown in FIGS. 5 and 6 above. The inner guide wire shaft 36 is bonded at its distal tip 34 to the distal end 32 of dilatation balloon 28. The proximal end 31 of dilatation balloon 28 may be bonded either to the distal end 22 of the outer 24 which defines the inflation lumen, or it may be bonded to a single catheter shaft 36 as shown in FIG. 6. Thus, the inner guide wire shaft 36 may be bonded to the outer member 28, 24 in predetermined, discrete locations.

In these embodiments, the outer member may be formed of the same material, but may be desirably formed of a second material which is different from the first. Suitable materials may be as those described above and include both elastomeric and non-elastomeric materials and include, but are not limited to, polyolefins such as polypropylene, polyethylene and so forth; polyolefin copolymers such as ethylene vinyl acetate; polyesters such as polyethylene terephthalate and phthalate polyesters and copolyesters; polyvinyl chlorides, ionomer resins; polyamides; nylons; polyester based elastomers such as polyester/polyether block copolymers including the HYTREL® series of polymers available from DuPont, ARNITEL® poly(butylene terephthalate)-block-poly(tetramethylene oxide) polymers available from DSM Engineering Plastics and polybutylene naphthalate-polyether block copolymers available from Teijin; polyamide elastomers such as polyamide-polyether-polyester block copolymers including PEBAX® 6333, 7033 and 7233 available from Elf Atochem, North America; polyurethane elastomers such as TECOFLEX® aliphatic polyurethane-polyether block copolymers and TECOTHANE® aromatic polyurethane-polyether polymers both available from Thermedics, Inc.; elastomeric polyurethane-polyethers and polyurethane-polyesters sold under the tradename of PELLETHANE® including 2102, 2103, 2202, 2353–2355 and 2363 available from Dow; other polyurethanes such as the ISOPLAST® series of polyurethanes available from Dow and TECOPLAST® series of aromatic polyurethane-polyethers available from Thermedics, Inc.; aromatic polyester polymers such as polyethylene terephthalate homopolymers and copolymers including TRAYTUF® 7357 and CLEARTUF® 8006 both available from Shell Chemical Co.; poly-n-propylene terephthalate, polybutylene terephthalate, polyethylene naphthalate; polybutylene naphthalate, and so forth; polycarbonate elastomers including the CARBOTHANE® series available from Thermedics; and so on and so forth.

Other elastomeric block copolymers may also find utility in the manufacture of the outer and/or inner members including styrene-butadiene-styrene, styrene-ethylene/propylene-styrene, styrene-ethylene/butylene-styrene, styrene-isoprenestyrene, styrene-isoprene, and so forth.

Any of the above described materials may be employed on both outer and inner members, although some are more suitable for the outer members and some are more suitable for the inner members depending on the properties desired. One of ordinary skill in the art understands the selection process, and also understands that this list is intended for exemplary purposes only and not as an exclusive list. There are numerous other polymers that may be employed in the invention herein and the invention is not intended to be limited in scope to those described above.

With reference to FIG. 5, prior to the present invention if a balloon 28 were made from a PEBAX® material and an inner guide wire shaft tubing 36 were made of a high density polyethylene (HDPE), the only effective way to obtain an effective bond between the balloon and shaft was to coextrude a PEBAX® material coating on the outside of tubing 36 for the entire length thereof. This may be undesirable in terms of material cost, added thickness and a possibility of the inner shaft to loose patency at body temperature. Use of a localized powder coated tie layer 30 which includes at least one maleated polyolefin, for instance PLEXAR® maleated polyolefin available from Quantum Chemical in Cincinnati, Ohio allows for a direct bonding of the Pebax® balloon 28 to a HDPE inner guide wire shaft 36 without requiring a Pebax® coextruded coating on the guide wire shaft. Optionally in this embodiment, the powder coated tie layer may also include a blend of PEBAX® and HDPE.

The powder coating composition may suitably include a single material which has compatibility with both substrates, or which may provide reasonable adhesion to both substrates as described above, or may include a blend of materials. The powder coating composition of the present invention may include any materials conventionally used in powder coating compositions. In addition to others, the polymeric materials described above find utility in the powder coating compositions of the present invention. When the powder coating composition is employed between two substrates which are dissimilar, it may be suitable to employ one polymeric material in the powder coating composition which exhibits compatibility with each of the substrates, or it may be suitable to employ a blend of polymeric materials as described above.

The powder coating may be applied using any powder coating techniques known in the art. Typically, such methods involve charging or ionizing the powder and then spraying it on a grounded surface or article in the presence of an applied electric field. The charged powder may be applied to the surface using any powder coating equipment known in the art such as that made by Nordsen or by Wagner including, for example, a Nordsen 2001 powder coating system or a Wagner EPG 2007 powder coating system.

An opposite charge is then applied to the coating composition used in the electrostatic coating process. The electrostatic attraction between the coating and the grounded substrate or article results in a more efficient coating process with less wasted material. When substrates are fabricated from metals, the metal, which is inherently conductive, is easily grounded and efficiently coated. However, when polymeric maerials are electrostatically coated, applying a charge is more difficult. This may be accomplished in any of a number of ways. In some instances, it may be advantageous to employ a surface treatment to which a charge may be applied. Such surface treatments are known to those of skill in the art. The surface treatment will then be exposed to an electric field wherein a charge is applied. The powder coating layer, having an opposite charge, is then applied to the surface treated substrate.

After application of the powder coating layer, the substrate to which it is applied may then be joined with a second substrate of the same or a different material. The entire assembly may then be thermally treated resulting in the formation of a thermal bond between the substrates. Typically, thermal treatment will involve the application of enough thermal energy to cuase the powder coating layer to flow. This temperature is typically just above the melting temperature of the powder. Such temperatures may be between about, for example, about 30° to about 400° C.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. An elongated medical device comprising:
   a) a first tubular member formed from polyethylene;
   b) a second tubular formed from a poly(ether-block-amide) copolymer; and
   c) a tie layer provided between said first tubular member and said second tubular member, said tie layer comprising a blend of melt polymers selected from the group consisting of polyethylene, poly(ether-block-amide), and maleated polyolefins.

2. The elongated medical device of claim 1 wherein said second tubular member overlaps at least a portion of said first tubular member, and said tie layer is provided in predetermined, discrete locations wherein said first and second tubular members overlap.

3. The medical device of claim 1 wherein said tie layer is provided between said first tubular member and said second tubular member at a lap joint bond between the first and second tubular members.

4. The medical device of claim 1 wherein said tie layer is provided between said first tubular member and said second tubular member at a butt joint bond between the first and second tubular members.

5. The medical device of claim 1 wherein said first tubular member is an inner or an outer catheter shaft, and said second substrate is an inner catheter shaft, an outer catheter shaft, a balloon distal tip or a hypotube.

6. The medical device of claim 1 wherein said first tubular member is an inner catheter shaft, said second tubular member is an inner catheter shaft and said proximal end of said first tubular member is joined to said distal end of said second tubular member by a lap joint or butt joint, and said powder coated tie layer is located between said first tubular member and said second tubular member at said lap joint or butt joint.

7. The medical device of claim 1 wherein said first substrate and said second substrate comprise at least one member selected from the group consisting of polyolefins, polyesters, polyethers, polyurethanes, polyureas, polyamides, nylons, poly(meth)acrylates, polymers of vinyl monomers, copolymers thereof, and mixtures thereof.

8. The medical device of claim 1 wherein said first tubular member comprises high density polyethylene, said second tubular member comprises a polyether block amide.

9. The medical device of claim 1 wherein said tie layer comprises a maleated polyolefin.

10. The medical device of claim 1 wherein said tie layer comprises a blend of high density polyethylene and polyether block amide.

* * * * *